United States Patent [19]
Roberts et al.

[11] Patent Number: 5,958,769
[45] Date of Patent: Sep. 28, 1999

[54] COMPOSITIONS AND METHODS FOR MEDIATING CELL CYCLE PROGRESSION

[75] Inventors: James M. Roberts; Steven R. Coats; Matthew L. Fero, all of Seattle, Wash.

[73] Assignee: Fred Hutchinson Cancer Research Center, Seattle, Wash.

[21] Appl. No.: 08/588,595

[22] Filed: Jan. 18, 1996

[51] Int. Cl.$^6$ ............... C12N 15/79; C12N 5/10; A01N 43/04; C07H 21/04
[52] U.S. Cl. ............ 435/375; 435/325; 435/320.1; 514/44; 536/23.1; 536/24.5
[58] Field of Search ............. 435/240.2, 240.26, 435/325, 375, 320.1; 424/93.21; 536/23.1, 24.5; 514/44

[56] References Cited

U.S. PATENT DOCUMENTS 5,302,706   4/1994   Smith ....................... 536/23.1

OTHER PUBLICATIONS

Rojanasakul, Y. Advanced Drug Delivery Reviews. 18:115–131, 1996.
Stull, RA et al. Pharmaceutical Research. 12(4):465–483, 1995.
Rivard, N et al. J. Biol. Chem. 27(31): 18337–18341, Aug. 2, 1996.
Ravitz, MJ et al. Cancer Res. 55: 1413–1416, Apr. 1, 1995.
Firpo, EJ et al. Mol. Cell Biol. 14(7); 4889–4901, Jul. 1994.
Polyak, K et al. Cell. 78: 59–66, Jul. 15, 1994.
Sorrentino, BP et al. Science. 257: 99–103, Jul. 3, 1992.
Fero et al., "A Syndrome of Multiorgan Hyperplasia with Features of gigantism, Tumorigenesis, and Female Sterility in p27$^{Kip1}$–Deficient Mice", *Cell* 85:733–744 (1996).
Kiyokawa et al., "Enhanced Growth of Mice Lacking the Cyclin–Dependent Kinase Inhibitor Function of p27$^{Kip1}$", *Cell* 85:721–732 (1996).
Nakayama et al., "Mice Lacking p27$^{Kip1}$ Display Increased Body Size, Multiple Organ Hyperplasia, Retinal Dysplasia, and Pituitary Tumors", *Cell* 85:707–720 (1996).
Tyers, "The cyclin–dependent kinase inhibitor p40$^{SIC1}$ imposes the requirement for Cln G1 cyclin function at Start", *Proc. Natl. Acad. Sci. USA* 93:7772–7776 (1996).

*Primary Examiner*—David Saunders
*Assistant Examiner*—F. Pierre VanderVegt
*Attorney, Agent, or Firm*—Townsend and Townsend and Crew LLP

[57] ABSTRACT

Inhibitors of the p27 cyclin dependent kinase inhibitor protein or sequences encoding the protein modulate vertebrate cell cycle progression and increase the proportion of dividing cells to non-dividing cells in a population of treated cells. As the proportion of dividing cells increases, the cell population, e.g., hematopoietic progenitor (stem) cells, is more efficiently used for gene therapy applications.

20 Claims, 2 Drawing Sheets

COMPOSITIONS AND METHODS FOR MEDIATING CELL CYCLE PROGRESSION

GOVERNMENT SUPPORT

The U.S. government may have certain rights in the invention pursuant to Grant No. CA 61352 received from the U.S. National Institutes of Health.

BACKGROUND OF THE INVENTION

Mammalian cells can shift from a proliferating state to a quiescent state only during a brief window of the cell cycle. Temin, *J. Cell. Phys.* 78:161 (1971). Thus, depending on their position in the cell cycle, cells deprived of mitogens such as those present in serum will undergo immediate cell cycle arrest, or they will complete mitosis and arrest in the next cell cycle. The transition from mitogen-dependence to mitogen-independence occurs in the mid- to late-G1 phase of the cell cycle. Pardee, *Proc. Natl. Acad. Sci.* 71:1286 (1974), showed that many different anti-mitogenic signals cause the cell cycle to arrest at a kinetically common point, and further showed that the cell cycle becomes unresponsive to all of these signals at approximately the same time in mid- to late-G1. This point was named the restriction point, or R point.

Time-lapse cinematography of mitotically proliferating single cells has also been used to precisely map the timing of the cell cycle transition to mitogen-independence. This confirmed that mitogen depletion or other growth inhibitory signals cause post-mitotic, early-G1 cells to immediately exit the cell cycle, and that cell cycle commitment (autonomy from mitogenic signals), occurs in mid-G1 (Larsson et al., *J. Cell. Phys.* 139:477 (1989), and Zetterberg et al., *Proc. Natl. Acad. Sci. USA* 82:5365 (1985)). Together these observations show that the mitogen-dependent controls on cell proliferation are linked to cell cycle progression.

Transit through G1 and entry into S phase requires the action of cyclin-dependent kinases (Cdks) (Sherr, *Cell* 79:551 (1994)). Growth inhibitory signals have been shown to prevent activation of these Cdks during G1 (Serrano et al., *Nature* 366:704 (1993); Hannon and Beach, *Nature* 371:257 (1994); El-Deiry et al., *Cell* 75:89 (1993); Xiong et al., *Nature* 366:701 (1993); Polyak et al., *Cell* 78:59 (1994); Toyashima and Hunter, ibid., p. 67; Lee et al., *Genes & Dev.* 9:639 (1995); Matsuoka et al., ibid., p. 650; Koff et al., *Science* 260:536 (1993)). The catalytic activity of Cdks is known to be regulated by two general mechanisms, protein phosphorylation and association with regulatory subunits (Gould et al., *EMBO J.* 10:3297 (1991); Solomon et al., ibid., 12:3133 (1993); Solomon et al., *Mol. Biol. Cell* 3:13 (1992); Jeffrey et al., *Nature* 376:313 (1995); Morgan, *Nature* 374:131 (1995)). Among the regulatory subunits, the association of Cdks with inhibitory CKI subunits (Cyclin-dependent Kinase Inhibitors) has been most closely correlated with the effect of mitogen depletion on cell proliferation and Cdk activity.

The CKI directly implicated in mitogen-dependent Cdk regulation is p27Kip1 (Polyak et al., *Cell* 78:59 (1994); Toyashima and Hunter, ibid., p. 677). The p27 protein accumulates to high levels in quiescent cells, and is rapidly destroyed after quiescent cells are re-stimulated with specific mitogens (Nourse et al., *Nature* 372:570 (1994); Kato et al., Cell 79:487 (1994)). Moreover, constitutive expression of p27 in cultured cells causes the cell cycle to arrest in G1 (Polyak supra, Toyashima and Hunter, supra).

Gene therapy is proposed for treating and preventing a wide variety of acquired and hereditary diseases, such as infectious diseases, cancer, etc. and relies on the efficient delivery of therapeutic genes to target cells. Most of the somatic cells that have been targeted for gene therapy, e.g., hematopoietic cells, skin fibroblasts and keratinocytes, hepatocytes, endothelial cells, muscle cells and lymphocytes, are normally non-dividing. Retroviral vectors, which are the most widely used vectors for gene therapy, unfortunately require cell division for effective transduction (Miller et al., *Mol. Cell. Biol.* 10:4239–4242 (1990)). This is also true with other gene therapy vectors such as the adeno-associated vectors (Russell et al., *Proc. Natl. Acad. Sci. USA* 91:8915–8919 (1994); Alexander et al., *J. Virol.* 68:8282–8287 (1994); Srivastrava, *Blood Cells* 20:531–538 (1994)). The majority of stem cells, a preferred target for many gene therapy treatments, are normally not proliferating. Thus, the efficiency of transduction is often relatively low, and the gene product may not be expressed in therapeutically or prophylactically effective amounts. This has led investigators to develop techniques such as pretreatment with 5-fluorouracil, infection in the presence of cytokines, and extending the vector infection period to increase the likelihood that stem cells are dividing during infection, but these have met with limited success.

What is needed in the art is a method for improving the efficiency of gene transfer that is useful for a wide variety of gene therapy applications. For example, what is needed is a means to improve transduction efficiency into a wide variety of vertebrate cells with vectors that can transduce only dividing cells by controlling key molecular events in the cell cycle commitment through the Restriction point and thus cell cycle progression. Quite surprisingly, the present invention fulfills this and other related needs.

SUMMARY OF THE INVENTION

The present invention provides compositions which comprise inhibitors of p27 that specifically increase the proportion of dividing cells to non-dividing cells in a population of cells. The inhibitors can substantially decrease or eliminate expression of p27 protein, thereby permitting activation of cyclin E-Cdk2 and/or cyclin A-Cdk2 complexes. Particularly useful are oligonucleotide inhibitors of p27, such as triplex forming oligonucleotides, an antisense oligonucleotides, and ribozymes.

Thus, in another embodiment the invention also provides isolated vertebrate cell populations which have been treated with a p27 inhibitor and have an increased proportion of dividing cells to non-dividing cells relative to the proportion in a population of untreated cells. Said dividing cells, e.g., hematopoietic progenitor cells, are particularly useful as targets of gene therapy, including the use of viral vectors that preferentially transduce dividing cells. Thus, the invention provides a method for increasing the efficiency of gene therapy techniques by increasing the number of cells which can be transduced and thereby increasing the availability of a desired gene product.

In other embodiments the invention provides methods for increasing the proportion of dividing cells in a vertebrate cell population. A population of cells is exposed to a p27 inhibitor in an amount sufficient to increase the proportion of dividing cells to non-dividing cells relative to said proportion in a population of untreated cells. Such cell population can be a substantially non-dividing or terminally differentiated primary cell population, including, e.g., fibroblasts, osteoblasts, myeloblasts, neurons or epithelial cells. Isolated hematopoietic progenitor cells are particularly useful in the present methods. The cells can be exposed to the inhibitor either in vitro or in vivo. When performed in vitro, the method can further comprise the step of administering the exposed cells to a host, particularly when the exposed cells have been transduced to express a desired gene. Thus, the method provides for increasing the efficiency of transducing a vertebrate cell population with a viral vector encoding a gene product of interest. The target cells, e.g., mammalian hematopoietic progenitor cells, are exposed to a p27 inhibitor in an amount sufficient to increase the percentage of dividing cells, and contacting the treated cells to a viral vector encoding the gene product of interest.

BRIEF DESCRIPTION OF THE DRAWINGS

FIG. 1 shows that p27 is required for cell cycle withdrawal, where

FIG. 2 shows that enforced p27 expression reverses the p27 antisense effect in serum starved cells, where

DESCRIPTION OF THE SPECIFIC EMBODIMENTS

Figure 1A:
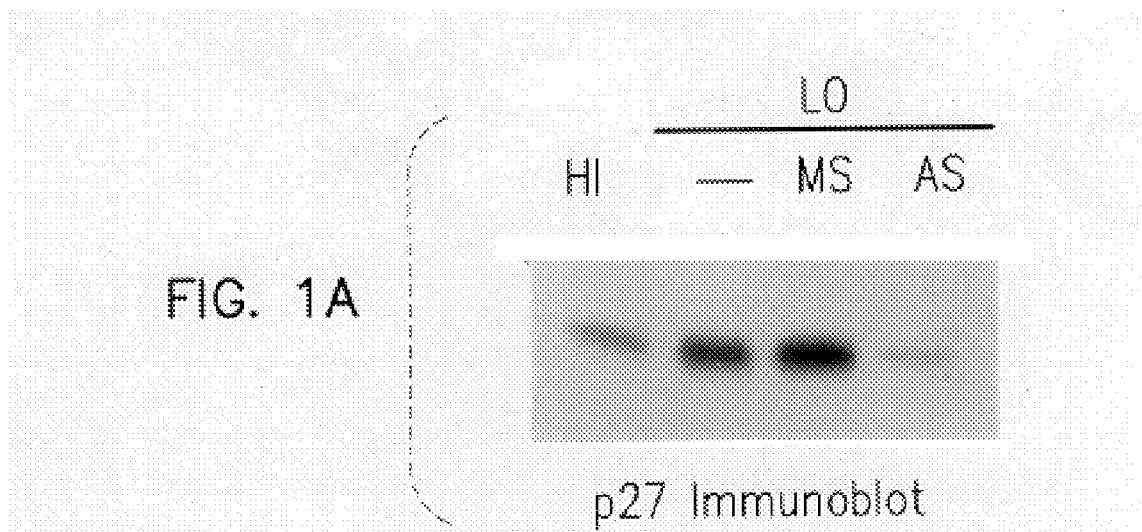
FIG. 1A is a p27 immunoblot analysis of extracts from control proliferating Balb/c-3T3 cells (Hi), subconfluent serum starved Balb/c-3T3 cells (Low) and subconfluent Balb/c-3T3 cells serum starved for 24 h following lipofection with either p27 mismatch (MS) or antisense (AS) oligonucleotides.

The present invention provides compositions and methods for increasing the proportion of proliferating cells in a cell population by exposing the cell population to an inhibitor of p27 activity. The mediator can be directed to a nucleic acid molecule which encodes the p27 protein, i.e., the p27 gene or RNA transcripts thereof, or to the p27 protein itself, or subunits thereof. The inhibitor is provided to the cell population under conditions and in an amount sufficient to permitting progression of the cell cycle in the treated cells, thereby increasing the percentage of dividing cells in the cell population relative to an untreated cell population.

p27 is a cellular protein having a molecular weight of about 27 kD that inhibits progression of the cell cycle through the Restriction point in early to mid-G1 phase. p27 acts by binding to and inhibiting the activation of cyclin E-Cdk2 and cyclin A-Cdk2 complexes. Characterization of the p27 protein and cloning and sequencing of the gene encoding the p27 protein are described in more detail in co-pending PCT application WO PCT/US95/07361, incorporated herein by reference.

Inhibitors of p27 are useful in the present invention to permit the activation of cyclin E-Cdk2 and cyclin A-Cdk2 complexes and the ensuing progression of the cell cycle through cell division. By maintaining p27 at sufficiently low levels repetitive cell cycling can be achieved. As the proportion of dividing cells in a given cell population increases, among other things the efficiency of transduction increases for viral vectors encoding desired gene products. Thus, the inhibitors are useful to overcome obstacles that have plagued gene therapy efforts. The inhibitors are particularly useful for increasing the population of dividing cells among hematopoietic stem cells, which represent a preferred target cell population for many gene therapy protocols.

p27 inhibitors that permit the activation of cyclin E-Cdk2 and/or cyclin A-Cdk2 complexes can be identified in a variety of screening assay formats. Inhibitors of p27-mediated activation of cyclin E-Cdk2 and/or cyclin A-Cdk2 in the presence of p27 can be screened, for example, using an assay in which test substances are exposed to suitable amounts of p27 protein, cyclin E and or cyclin A, and Cdk2 under conditions that permit the formation of active cyclin E- or cyclin A-Cdk2 complexes in the absence of p27. The active cyclin E- and/or cyclin A-Cdk2 complexes formed are then quantitated and compared to the active complexes formed in the absence of the test substance.

Substances which can serve as p27 inhibitors include, but are not limited to, compounds capable of inhibiting the p27-mediated inhibition of cyclin E-Cdk2 complex activation, compounds that specifically inhibit the interaction between p27 and cyclin E-Cdk2 complexes and/or between p27 and cyclin A-Cdk2 complexes, but not the site-specific phosphorylation of the Cdk2 moiety of the cyclin-Cdk2 complex in the absence of p27, compounds that degrade or inactivate the p27 protein, and compounds that interfere with the expression of p27 protein. Such agents may include chemical compound inhibitors of p27, protein or peptide p27 antagonists, and molecules that inhibit the expression of p27 such as triplex forming oligonucleotides, antisense oligonucleotides, ribozymes, etc.

For use as p27 inhibitors in the present invention to mediate cell cycle progression, the triplex forming oligonucleotides are p27 sequence-specific DNA binding drugs that interfere with p27 transcription. Triplex-forming oligonucleotides are generally described in Maher, *Bioessays* 14:807–815 (1992); Gee et al., *Gene* 149:109–114 (1994); Noonberg et al., *Gene* 149:123–126 (1994); Song et al., *Ann. NY Acad. Sci.* 761:97–108 (1995); Westin et al., *Nuc. Acids. Res.* 23:2184–2191 (1995); and Wand and Glazer, *J. Biol. Chem.* 207:22595–22901 (1995). These oligonucleotides form triple helical complexes, under physiological conditions, on double-stranded DNA selectively inhibiting p27 transcription by physically blocking RNA polymerase or transcription factor access to the p27 DNA template. See also, e.g., WO 95/25818; WO 95/20404; WO 94/15616; WO 94/04550; and WO 93/09788, each of which is incorporated herein by reference. The triplex forming oligonucleotides targeted to the p27 gene may contain either a nucleotide or non-nucleotide tail to enhance the inhibition of transcription factor binding.

Antisense oligonucleotides that interfere with the expression of p27 and permit progression of the cell cycle, as exemplified in the Examples described hereinbelow, are particularly useful in the present invention. p27 antisense inhibitors are identified using methods, e.g., as described in detail in the Examples. The use of antisense oligonucleotides and their applications are described generally in, for example, Mol and Van der Krul, eds., *Antisense Nucleic Acids and Proteins Fundamentals and Applications*, New York, N.Y., 1992, which is incorporated by reference herein in its entirety. Suitable antisense oligonucleotides are at least 11 nucleotide in length and up to and including the upstream untranslated and associated coding sequences of p27. As will be evident to one skilled in the art, the optimal length of antisense oligonucleotides is dependent on the strength of the interaction between the antisense oligonucleotides and their complementary sequence on the mRNA, the temperature and ionic environment translation takes place, the base sequence of the antisense oligonucleotide, and the presence of secondary and tertiary structure in the mRNA and/or in the antisense oligonucleotide. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotide is the 5' untranslated region of the p27 gene.

Antisense oligonucleotides targeted to the p27 gene are prepared by inserting a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense oligonucleotides. Alternatively, antisense oligonucleotides may be synthesized using standard manual or automated synthesis techniques. Synthesized oligonucleotides may be introduced into suitable cells by a variety of means including electroporation (e.g., as described in Yang et al., *Nucl. Acids. Res.* 23:2803–2810 (1995)), calcium phosphate precipitation, microinjection, poly-L-ornithine/DMSO (Dong et al., *Nucl. Acids. Res.* 21:771–772 (1993)). The selection of a suitable antisense oligonucleotide administration method will be evident to one skilled in the art. With respect to synthesized oligonucleotides, the stability of antisense oligonucleotides-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates or phosphorodithioates. Oligonucleotides may also be made nuclease resistant by the synthesis of the oligonucleotides with alpha-anomers of the deoxyribonucleotides, as generally described in Mol and van der Krul, supra.

For oligonucleotide-based inhibitors, the choice of a suitable sequence will be guided by, for example, the type of inhibitor (i.e., triplex forming oligonucleotide or antisense oligonucleotide) and the species to be treated. It may be preferable to choose sequences that are conserved between species to permit use in readily available animal models. As shown in more detail below, antisense oligonucleotides to sequences within p27 that are conserved between mouse and human were chosen for use in the mouse model. Such sequences may then be used in human cells without reformulation.

The present invention also provides compositions and methods for inhibiting p27 and thereby permitting cell cycle progression using ribozymes. The ribozymes can be administered in a variety of ways, including by gene therapy targeted to a desired cell. A ribozyme of the invention targets the RNA transcripts of the p27 gene. Each ribozyme molecule contains a catalytically active segment capable of cleaving the p27 RNA, and further comprises flanking sequences having a nucleotide sequence complementary to portions of the targeted RNA. The flanking sequences serve to anneal the ribozyme to the RNA in a site-specific manner. Absolute complementarity of the flanking sequences to the target p27 sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific p27 RNA target, and also has enzymatic activity that is active to cleave and/or splice RNA in that target, thereby altering the target molecule. In preferred embodiments of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8:183 (1992), hairpin motifs are described by Hampel et al., *Biochem.* 28:4929 (1989) and Hampel et al., *Nucl. Acids Res.* 18:299 (1990), the hepatitis delta virus motif is exemplified in Perrotta and Been, *Biochem.* 31:16 (1992), an RNAseP motif is described in Guerrier-Takada et al., *Cell* 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target p27 RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 9 to 12, and results in base pairing to the substrate sequence immediately upstream and downstream of the p27 RNA sequences which comprise the cleavage site.

The p27 inhibitors may be used alone or in combination may be formulated for a variety of modes of administration. Administration of the inhibitors may include systemic, topical or local administration. Techniques and formulations are generally described in *Remington's Pharmaceutical Sciences,* Mack Publishing Co., Easton, Pa., latest edition. The inhibitor is generally combined with a pharmaceutically acceptable carrier such as a diluent or excipient. Suitable carriers may include fillers, extenders, binders, wetting agents, disintegrants, surface-active agents or lubricants. The choice of such ingredients will depend on the mode of administration and dosage forms. Typical dosage forms include tablets, powders, liquid preparation including suspensions, emulsions, and solutions, granules, capsules and suppositories. Liquid preparation for injection are also typical and include liposome preparations.

A sequence comprising or encoding an oligonucleotide p27 inhibitor, e.g., triplex forming oligonucleotides, antisense oligonucleotide, ribozyme, etc., or a combination of such inhibitors targeted to different portions of the p27 DNA or corresponding RNA can be delivered in a wide variety of ways to targeted cells to facilitate progression of the cell cycle. The oligonucleotides can be administered as synthetic oligonucleotides or expressed from an expression vector.

The oligonucleotide can be administered ex vivo, i.e., contacted with target cells that have been removed from an individual or other cell source, treated and returned, or the oligonucleotide molecule can be administered in vivo. When administered ex vivo typically the target cells are exposed to mitogens, e.g., serum mitogens (SCF, IL-3, EPO, TPO, etc.) or the like depending on particular cell population.

Delivery to the targeted cell population can be via an appropriate delivery vehicle, e.g., a liposome, a controlled release vehicle, by use of iontophoresis, electroporation or ion paired molecules, or covalently attached adducts, and other pharmacologically acceptable methods of delivery. Preferably a carrier provides a means to accumulate the oligonucleotide within or at a desired cell population. The delivery vehicle can be designed to serve as a slow release reservoir or to deliver its contents directly to the target cell. Examples of oligonucleotide delivery vehicles include liposomes, hydrogels, cyclodextrins, biodegradable nanocapsules, and microspheres. Liposomes can readily be targeted to the various tissues or cell populations. In another embodiment the anti-p27 oligonucleotide is administered via an expression vector that is suitable for delivery and expression of an oligonucleotide comprising said oligonucleotide in a mammalian host cell.

For in vivo use, routes of oligonucleotide administration include intramuscular, aerosol, intravenous, parenteral, intraperitoneal, etc. The specific delivery route for a selected oligonucleotide will depend on a variety of factors, such as the form of the oligonucleotide, the intended target, the condition being treated, etc. For example, while unmodified oligonucleotide is taken up by cells, modifications can be made to enhance cellular uptake, e.g., by reducing the oligonucleotide's charge to produce a molecule which is able to diffuse across the cell membrane. The structural requirements necessary to maintain oligonucleotide activity are generally recognized in the art. Modifications to enhance cellular delivery can also be designed to reduce susceptibility to nuclease degradation.

The dosage of oligonucleotide inhibitor will also depend on a variety of factors, such as the form of the oligonucleotide, the route of administration, the stage of the cell cycle, the percentage of non-dividing cells in a selected population, whether terminal differentiation has been reached, etc., and thus can vary widely. Generally the dosage will result in complete inhibition of p27 activity or levels sufficiently low within the targeted cells sufficient to permit activation of the cyclin E- and/or cyclin A-Cdk2 complexes and progression of the cell cycle. Establishment of effective levels of p27 inhibitor within a targeted cell population depends upon, e.g., the rate of uptake (or expression by a particular vector), and rate at which the inhibitor is degraded. The duration of treatment may extend for a time sufficient to permit, e.g., transduction of a relatively high percentage of dividing cells compared to an untreated control cell population, but usually will be at least for about 2–4 days, sometimes 6–10 days, although longer durations may be necessary for quiescent or terminally differentiated cell populations. The number and timing of doses can vary considerably, depending on the factors discussed above and the efficacy of a particular inhibitor or mixture thereof, the delivery vehicle and route of administration, etc.

For nucleotide inhibitors of p27 such as p27 antisense oligonucleotides or p27-specific triplex forming oligonucleotides, it may be preferable in include an effective concentration of a lipid formulation with the oligonucleotide of the present invention. Suitable lipid formulations and concentrations are those that enhance the uptake of the oligonucleotides by cells. Such lipids include cationic lipids used for lipofection such as N-[1-(2,3-dioleyloxy)propyl-N,N,N-trimethylammonium chloride (DOTMA) and dioleoyl phophatidylethanolamine (DOPE). One skilled in the art may determine the particular lipid formulation or concentration that will be effective for enhancing the uptake of the oligonucleotide.

Within the methods described in detail herein, the p27 inhibitors may be used in combination with other compounds that inhibit cells from entering cell cycle arrest or which inhibit differentiation that may accompany the proliferation of certain cells. Retinoic acid receptor antagonists, for example, may be used in combination with the disclosed methods and compositions to increase the number of proliferating cells in a cell population. The retinoic acid receptor α antagonist Ro 41–5253 (Apfel et al., *Proc. Natl. Acad. Sci. USA* 89:7129–7133, 1992) has been shown to counteract the retinoic acid-induced differentiation of the promyelocytic cell line HL-60. Alternatively, antagonists of mitotic inhibitors such as p14 (Guan et al., *Genes Dev.* 8:2939–2952 (1994)), p15 (Hannon and Beach, *Nature* 371:257–261 (1994)), p16 (Okamoto et al., *Cancer Research* 55:1448–151 (1995) and Serrano et al., *Nature* 366:704–707 (1993)), p18 (Guan et al., ibid.), p19 (Chan et al., *Mol. Cell. Biol.* 15:2682–2688 (1995) and Zhang et al., *Cell* 82:915–925 (1995)) and p21 (Harper et al., *Cell* 805–816 (1993) may be used in combination with the p27 inhibitors of the present invention to increase the proportion of proliferating cells in a cell population. Antagonists of these mitotic inhibitors include, but are not limited to, agents that interfere with the transcription or translation of the inhibitors, destruction of the protein, and direct inhibitors of the protein. As such, inhibitors of mitotic inhibitors may include chemical compound inhibitors of the mitotic inhibitors, protein or peptide mitotic inhibitor antagonists, triplex forming oligonucleotides and antisense molecules that inhibit the expression of the mitotic inhibitors, ribozymes, etc.

The methods of the present invention are particularly useful for gene therapy. Target cells for gene therapy are exposed to p27 inhibitors under suitable conditions and for a time sufficient to increase the proportion of dividing cells in the target cell population. The dividing cells are then exposed to a suitable viral vector comprising a gene of interest. Within one embodiment, the cells are exposed to the p27 inhibitor and the viral vector concurrently. Suitable viral vectors include retroviral vectors (see Miller, *Curr. Top. Microbiol. Immunol.* 158:1–24 (1992); Salmons and Gunzburg, *Human Gene Therapy* 4:129–141 (1993); Miller et al., *Methods in Enzymology* 217:581–599, (1994)) and adeno-associated vectors (reviewed in Carter, *Curr. Opinion Biotech.* 3:533–539 (1992); Muzcyzka, *Curr. Top. Microbiol. Immunol.* 158:97–129 (1992)). Other viral vectors that may be used within the methods include adenoviral vectors, herpes viral vectors and Sindbis viral vectors, as generally described in, e.g., Jolly, *Cancer Gene Therapy* 1:51–64 (1994); Latchman, *Molec. Biotechnol.* 2:179–195 (1994); and Johanning et al., *Nucl. Acids Res.* 23:1495–1501 (1995), each incorporated herein by reference). The choice of vector will rely in part on the cell type targeted, the disease state that is being treated and the size of the gene to be transferred.

Cells which are exposed to a p27 inhibitor in an amount and for a time sufficient to inhibit exit from the cell cycle can be treated by a variety of substances that target dividing cells. In one embodiment, for example, a cell population in which the proportion of dividing cells has been increased by a p27 inhibitor are more efficiently transduced or transfected with a nucleotide sequence encoding a gene product of interest. Thus, the methods described herein increase the efficiency of gene therapy techniques. For example, target cells treated with a p27 inhibitor are transduced with at least one gene encoding an expression product of interest, typically an RNA or protein molecule. The encoded RNA or protein is one which confers a benefit to the cell population or host being treated, either directly or indirectly. The gene may encode a secreted or non-secreted protein, or an active portion thereof. The selection of a suitable gene for the condition being treated will depend on the condition being treated or prevented and other factors apparent to those skilled in the art. By "gene" is meant DNA that encodes a desired product, such as, for example, a cytokine, a clotting factor, a hormone, an enzyme, a transport protein, a regulatory protein, a structural protein, a receptor, an antigen, ribozyme, antisense molecule, etc. Representative examples of genes for introducing into humans are those encoding human erythropoietin (described in U.S. Pat. No. 4,703,008), human G-CSF, human GM-CSF (Anderson et al., *Proc. Natl. Acad. Sci. USA* 82:6250 (1985)), plasminogen activator, urokinase, insulin (e.g., human insulin as described in U.S. Pat. No. 4,652,525 or proinsulin described in U.S. Pat. No. 4,431,740), interleukins (e.g., interleukin-1, interleukin-2 [described in U.S. Pat. No. 4,738,927], interleukin-3 [described in EP Publ. 275,598 and 282,185], interleukin-4, interleukin-7 [U.S. Pat. No. 4,965,195], etc.), interferons, Factor VIII, Factor IX, von Willebrand Factor, ADA, human growth hormone (described in U.S. Pat. No. 4,342,832), etc., analogs and fusions thereof (e.g., fusions of GM-CSF and IL-3[U.S. Pat. No. 5,108,910]. Each of the foregoing patents and publications is expressly incorporated herein by reference.

It is possible and may be desirable in some instances to employ a mixture of cells treated with a p27 inhibitor, which include a first group transduced with a gene of interest and a second group transduced with a second, different gene of interest. Alternatively, the treated cells may be transduced with more than one gene of interest.

The genes are transduced or transfected into the target cell population which has been treated with a p27 inhibitor using well established protocols. Typically the gene transfer vector will be a retroviral vector, but other vectors may also be employed, e.g., adenovirus vectors (e.g., Rosenfeld et al., *Cell* 68:143–155 (1992) and Curiel et al., *Proc. Natl. Acad. Sci. USA* 88:8850–8854 (1991), adenovirus associated vectors (e.g., Muzyczka, *Curr. Top. Microbiol. Immunol.* 158:97–129 (1992), and as reviewed by Miller, *Nature* 357:455–460 (1992), which publications are incorporated herein by reference). The construction of retroviral vectors has been described, e.g., Miller and Rosman, *Biotechniques* 7: 980–990 (1989); Adam et al., *J. Virol.* 65:4985–4990 (1991); Miller, *Curr. Top. Microbiol. Immunol.* 158:1–24 (1992); and UK Patent Publication GB 2,269,175A, each of which is incorporated herein by reference. A preferred retroviral vector is made using PA317 amphotropic retrovirus packaging cells, as described in Miller, U.S. Pat. No. 4,861,719, incorporated herein by reference.

When the cell population treated with p27 inhibitor is transduced or transfected ex vivo with a gene of interest, cells containing the desired gene(s) are often cultured, typically in the presence of a selection agent, e.g., G418, neomycin or the like depending on the selectable marker used in the vector, and then may be returned to the host or expanded until a sufficient number of cells are available for return to the host.

The compositions and methods of the present invention are used to treat a wide variety of cell types. Among those most often targeted for gene therapy are hematopoietic precursor (stem) cells. Other cells include those of which a proportion of the targeted cells are nondividing or slow dividing. These include, for example, fibroblasts, keratinocytes, endothelial cells, skeletal and smooth muscle cells, osteoblasts, neurons, quiescent lymphocytes, terminally differentiated cells, slow or non-cycling primary cells, etc. The methods and compositions can be employed with cells of a wide variety of vertebrates, including mammals, and especially those of veterinary importance, e.g., canine, feline, equine, bovine, ovine, caprine, rodent, lagomorph, swine, etc., in addition to human cell populations.

The present invention is particularly preferred for increasing the proportion of dividing cells in a population of hematopoietic precursor cells, especially those of human and other mammals, either ex vivo or in vivo. In an ex vivo method, hematopoietic precursor cells are separated from a blood product, such as bone marrow, peripheral blood, or umbilical cord blood of a donor, fetal peripheral blood and other sources. Such separation may be performed, for example, by immunoselection on the basis of their expression of an antigen, such as the CD34 antigen which is present on substantially all human hematopoietic precursor cells, but is substantially absent from more mature hematopoietic cells. The separated hematopoietic precursor cells may be stored frozen and thawed at a later date for inoculation into a suitable vessel containing a culture medium comprising a nutritive medium. Alternatively, the separated cells may be inoculated directly into culture without first freezing. In both cases the resultant cell suspension is cultured with a p27 inhibitor as described herein under conditions and for a time sufficient to increase the proportion of dividing hematopoietic precursor cells relative to the proportion of such cells present initially in the blood product. The cells may then be treated with vector capable of expressing the gene product of interest. The cells may then be infused or implanted into a host or stored frozen for infusion at a later date.

In addition, the methods of the present invention may be used in vitro to create novel stem cell lines. According to this aspect of the invention the p27 inhibitor is administered to a cell population, thereby preventing cells from exiting the cell cycle and increasing the percentage of cells in the cell cycle, and may also reduce the need to include exogenous serum mitogens. The methods may also be used in combination with, for example, methods for creating stem cell lines by exposing the cell population to a p27 antagonist under suitable conditions and for a time sufficient to increase the population of dividing cells, and exposing the dividing cells to a suitable expression vector comprising an gene encoding a desired gene product such that the resulting cells express the gene product and are self-renewing.

The following examples are offered by way of illustration, not by way of limitation.

EXAMPLE I

Subconfluent, exponentially asynchronous proliferating Balb/c-3T3 fibroblasts (Rb wild type; p53 status unknown) in media containing 10% fetal calf serum were rinsed once with serum-free medium and transferred to low serum medium containing mitogens (0.1% serum). Flow cytometry analysis (Firpo et al., *Mol. Cell. Biol.* 14:4889 (1994)) demonstrated that within 24 hours, approximately the length of one cell cycle, 95% of the cells arrested in G1, indicating that these cells require a mitogenic signal to proceed through each division cycle. G1 arrest correlated with a 6 to 8 fold induction of the p27$^{Kip1}$ protein as determined by immunoblot analysis (Nourse et al., *Nature* 372:570 (1994); Kato et al., *Cell* 79:487 (1994)) of proliferating and serum-starved cells. Similar increases in p27 expression occur in primary human diploid fibroblasts deprived of serum mitogens, and in primary human T lymphocytes following withdrawal of IL-2, indicating that this is a common pattern of p27 expression in normal, non-transformed cells (Nourse, ibid., Kato, ibid.).

It was then shown that in Balb/c-3T3 cells p27 levels start to increase within 4 hours of serum withdrawal, reach 60% of maximal levels within 12 hours, and peak by 24 hours. Proliferating Balb/c-3T3 fibroblasts were rinsed in serum-free medium and re-fed with low serum medium containing 0.1% serum. p27 western blots (ECL, Amersham) were performed on cells harvested at 4, 8, 12, 16 and 24 hours after re-feeding. p27 levels started to increase at 4 hours and were 60% of maximal at 12 hours). Thus, the induction of p27 protein parallels the accumulation of the initially asynchronous cell population in G1, , and indicates a critical role in the early events associated with exit from the cell cycle.

Histone H1 kinase assays were performed on cyclin A, cyclin E and Cdk2 (Firpo et al., *Mol. Cell. Biol.* 14:4889 (1994)) immunoprecipitated from extracts made from proliferating and serum-starved Balb/c-3T3 cells. The results showed that cell cycle arrest of Balb/c-3T3 cells was correlated with downregulation of the cyclin E-Cdk2 and cyclin A-Cdk2 protein kinases, and this appeared to be related to induction of p27. Both cyclin E-Cdk2 and cyclin A-Cdk2 were associated with increased amounts of p27 following mitogen withdrawal. Immunodepletion experiments were also performed to determine the amount of cyclin E bound to p27. Cell extracts from asynchronously proliferating Balb/c-3T3 cells and Balb/c-3T3 cells that had been serum-starved for 24 hours were depleted for p27 by incubating 100 ug of each extract with p27 antiserum and protein A agarose for 1 hour at 4° C., centrifuging the immunoprecipitates for 5 seconds at 13,000 r.p.m and immunodepleting the remaining unbound supernatant twice more with p27 antiserum and protein A agarose. The immunodepleted extracts (α p27) were analyzed by cyclin E (Ohtsubo and Roberts, *Science* 259:1908 (1993); Matsushime et al., *Cell* 65:701 (1991); Koff et al., *Science* 257:1689 (1992)) and p27 immunoblots and compared to undepleted extracts and extracts depleted with p27 preimmune sera. The results showed that only a small portion of cyclin E in proliferating cells was bound to p27, while all the cyclin E in arrested cells was bound to p27. Similar results were obtained for cyclin A: Experiments were performed as for cyclin E, except that cyclin A and p27 immunoblots were performed on extracts depleted for p27. All of the cyclin A was bound to p27 in extracts from serum-starved cells while only a small fraction (5%) of cyclin A was associated with p27 in proliferating cells).

In sum, Balb/c-3T3 fibroblasts arrest in the first G1 following mitogen withdrawal, and this correlates with increased expression of p27, increased association of p27 with cyclins E and A, and inactivation of the cyclin E- and cyclin A-Cdk2 kinases.

The relationship between p27 expression and cell proliferation was studied by testing the relative abilities of specific serum mitogens to both downregulate p27 and induce cell proliferation. Flow cytometry analysis was performed on both the asynchronously proliferating Balb/c-3T3 cells (Hi serum) and subconfluent Balb/c-3T3 cells that had been serum-starved for 24 hours (Low serum) in the presence of either individual growth factors (PDGF, IGF-1 or EGF) or all three growth factors (PIE) (see Table). p27 immunoblots were performed on cell extracts (10 ug) from cells treated with growth factors. Only PDGF was able to prevent G1 arrest, and only PDGF prevented the induction of p27. Balb/c-3T3 fibroblasts grown at high density have more complex mitogen requirements than when grown subconfluently; no single mitogen is able to cause proliferation of cells at high density. Instead, PDGF initially stimulates the density arrested, quiescent cells to become "competent" to respond to "progression" factors, IGF-1 and EGF (Pledger et al., *Proc. Natl. Acad. Sci. USA* 74:4481 (1977); Leof et al., *Exp. Cell Res.* 147:202 (1983)). Therefore, under these conditions passage through the restriction point does not occur until cells have been exposed to all three mitogens.

It was also observed that in density-arrested cells PDGF alone was insufficient to alter p27 abundance; rather p27 levels declined once cells became committed to proliferate in response to the complete mitogenic signal provided by the combined action of PDGF, EGF and IGF-1. Density-arrested Balb/c-3T3 fibroblasts were rinsed in serum-free medium and were re-fed with low serum medium containing 0.1% serum and 10 ng/ml of either PDGF, IGF, EGF, IGF and EGF, or all three growth factors. Cells were harvested 24 hours later and were analyzed by flow cytometry for DNA content and also by p27 immunoblot. The results indicated that a combination of all three growth factors was required to stimulate 70% of the cells to enter the cell cycle and to decrease p27 levels by ten-fold.

Thus, under two different growth arrest conditions the ability of specific mitogens to stimulate passage through the restriction point correlated with their ability to regulate p27. These results showed that p27 is not necessarily a downstream effector for any particular mitogen. Rather, decreased expression of p27 reflects the integrated action of the collection of mitogens required for cell proliferation.

EXAMPLE II

The observed correlation between p27 regulation and mitogenic signaling was extended by using anti-sense oligonucleotides to block expression of the p27 protein. This showed that regulation of p27 was necessary for cell cycle control by serum mitogens.

Phosphorothioate oligonucleotides were modified by the addition of a propyl group to the pyrimidine bases, which is thought to enhance base stacking and facilitate the sense-antisense interaction (Raviprakash et al., *J. Virol.* 69:69 (1995)). The oligonucleotides were synthesized by the H-phosphonate method on an automated synthesizer (model 8750, Milligen Bioresearch, Bedford, Mass.) using standard chemistry on controlled pore glass (CPG) support. The nucleoside analogs were prepared as previously described (B. Froehler, Protocols for Oligonucleotides and Analogs: Synthesis and Properties. Humana, Totowa, N.J. (1993); Froehler et al., *Tetrahedron Lett.* 33:5307 (1992); and Froehler et al., *Tetrahedron Lett.* 34: 1003 (1993)). The antisense oligonucleotides were designed to target sequences that are identical between the mouse and the human p27 sequences, which are described in WO PCT/US95/07361 and deposited with Genbank under accession nos. U09968 and U10906, respectively.

The antisense oligonucleotide sequences used in these experiments oligonucleotide 3163 ([SEQ ID NO:1] 5' UGG CUC UCC UGC GCC 3') (targets base pair 306–320 of murine Kip1, the sequence of which is described in WO PCT/US95/07361, incorporated herein by reference, and is also deposited with Genbank under Accession Number U09968) and its mismatch control oligonucleotide 3436

([SEQ ID NO:2] 5' UCC CUU UGG CGC GCC 3'), and oligonucleotide 3162 ([SEQ ID NO:3] 5' GCG UCU GCU CCA CAG 3') (targets base pair 548–562 of murine Kip1, the sequence of which is described in WO PCT/US95/07361, incorporated herein by reference and deposited with Genbank under Accession Number U09968) and its mismatch control oligonucleotide 3437 ([SEQ ID NO:4] 5' GCA UCC CCU GUG CAG 3'). The mismatch control oligonucleotides were designed to have the same base composition as the antisense oligonucleotides but with scrambled nucleotide sequences.

Oligonucleotides were efficiently delivered to cells by association with a lipophilic reagent, dioleoyl phosphotidylethanolamine (DOPE). For the lipofection procedure 30 nM of each oligonucleotide was mixed with 2.5 ug/ml of DOPE (2:1) (Gilead Sciences, Inc., Foster City, Calif.) in serum-free medium and incubated for 10 minutes at 37° C. Proliferating Balb/c-3T3 fibroblasts were rinsed once in serum-free medium and re-fed with the oligonucleotide/DOPE solution in low serum medium containing 0.1% serum. The cells were then incubated for 24 hours in humidified incubators at 37° C. with 5% $CO_2$.

The percentage of cells that took up the oligonucleotides was determined by lipofecting proliferating Balb/c-3T3 cells with an FITC-tagged random oligonucleotide (Gilead Sciences, Inc.) for 6 hours with subsequent re-feeding with low serum medium containing 0.1% serum for 24 hours. The percentage of cells that were positive for uptake of the FITC-tagged oligonucleotides was determined by UV fluorescent microscopy. The use of the FITC-labeled oligonucleotide control showed that 90–95% of the cells took up and concentrated the oligonucleotides in the cell nucleus.

Cell extracts from the serum-starved (24 hours in low serum medium containing 0.1% serum) Balb/c-3T3 fibroblasts transfected with the p27 antisense or mismatch control oligonucleotides were analyzed by immunoblotting with anti-p27 antiserum. The immunoblots showed that expression of p27 protein was substantially decreased in the antisense treated cells (FIG. 1A) while the mismatch oligonucleotide had no effect on accumulation of p27 following serum withdrawal. While the results were shown for one antisense and one control oligonucleotide, identical results were obtained with the other antisense and control oligonucleotides.

p27 antisense treatment did not decrease expression of the related CKI, p21. Proliferating Balb/c-3T3 fibroblasts were lipofected with antisense and mismatch oligonucleotides as described above. Cells were re-fed with low serum medium containing 0.1% serum and were analyzed 24 hours later by flow cytometry and p21 immunoblots. As observed in Firpo et al., Mol. Cell. Biol. 14:4889 (1994), p21 levels were elevated in proliferating cells as compared to serum-starved cells. Cells lipofected with either p27 mismatch or antisense oligonucleotides expressed slightly higher levels of p21 as compared to serum-starved control cells.

Figure 1B:
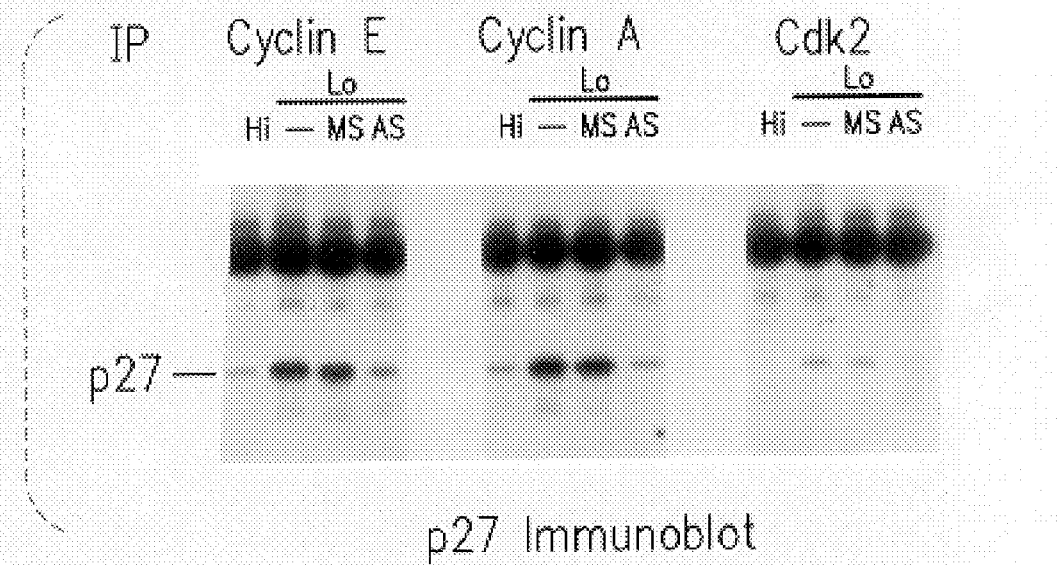
FIG. 1B is a p27 immunoblot analysis of cyclin A, cyclin E or Cdk2 immunoprecipitates from proliferating Balb/c-3T3 cells (HI), subconfluent serum starved Balb/c-3T3 cells (Lo) or Balb/c-3T3 cells serum starved for 24 h following lipofection with either mismatch (MS) or p27 antisense oligonucleotides (AS).

A decrease in the association of p27 with cyclin A and cyclin E corresponded to the decrease in overall levels of p27 in the antisense-treated cells (FIG. 1B). This was associated with restoration of cyclin E and cyclin A-associated kinase activities in serum-starved cells. Proliferating Balb/c-3T3 fibroblasts were lipofected with either p27 mismatch or antisense oligonucleotides for 6 hours and were then re-fed with low serum medium containing 0.1% serum. 24 hours later the cells were harvested, and Histone H1 kinase assays were performed on cyclin E and cyclin A immunoprecipitates. Serum-starved cells lipofected with p27 antisense oligonucleotides contained elevated levels of cyclin E and cyclin A associated Histone H1 kinase activity as compared to serum-starved cells.

In a proliferating population of Balb/c-3T3 fibroblasts 27% of the cells are in S phase, and this falls to about 9% of cells within 24 hours following serum withdrawal (Table). Flow cytometry of subconfluent Balb/c-3T3 cells serum-starved for 24 hours after lipofection with either p27 mismatch or antisense oligonucleotides as described above showed that cells exposed to the mismatch oligonucleotide behaved identically to control cells. However, cells exposed to p27 antisense oligonucleotides did not undergo G1 arrest after serum withdrawal; 23% of the cells remained in S phase (Table). p27 antisense oligonucleotides also prevented the osteosarcoma cell line SAOS-2 (Rb mutated; p53 mutated) from exiting the cell cycle in response to serum withdrawal (Table). This demonstrated that the requirement for p27 is manifest in more than one cell type, and that p27 is required for mitogen responsiveness independently of the Rb status of the cell.

TABLE

Data for experiments using flow cytometry. Flow cytometry analysis was performed as described in Firpo et al., Mol. Cell. Biol. 14:4889 (1994). The data are presented as the percentage of cells in each phase of the cell cycle.

| Cell Type/Condition | % | | |
| --- | --- | --- | --- |
| | G1 | S | G2/M |
| Balb/c-3T3 | | | |
| Hi Serum | 63.7 | 27.4 | 8.9 |
| Low serum | 86.9 | 9.3* | 3.9 |
| MSM/Lo | 81.7 | 11.6 | 6.7 |
| AS/Lo | 62.2 | 23.4 | 14.4 |
| MSM/Hi | 59.2 | 26.8 | 14.1 |
| AS/Hi | 42.3 | 35.1 | 22.6 |
| PDGF | 69.4 | 21.4 | 9.2 |
| IGF | 83.2 | 7.7 | 9.1 |
| EGF | 90.5 | 3.4 | 6.1 |
| PDGF/IGF/EGF | 64.2 | 23.8 | 11.9 |
| SAOS-2 | | | |
| Hi Serum | 54.3 | 25.8 | 19.9 |
| Low Serum | 70.6 | 13.6 | 15.8 |
| MSM/Lo | 60.5 | 16.8 | 22.7 |
| AS/Lo | 44.2 | 27.9 | 27.9 |

*Flow cytometry analysis overestimated the percentage of cells in S phase. BrdU staining demonstrated that under low serum conditions 25% of the cells were in S phase.

Incorporation of bromodeoxyuridine (BrdU, Amersham) and tritiated thymidine into nuclear DNA were used as independent measures of the effect of p27 antisense on cell cycle progression. Twenty-four hours after serum starvation Balb/c-3T3 cells that had been transfected with either the p27 antisense or mismatch oligonucleotides were pulse-labeled with BrdU for three hours to measure the fraction of cells continuing to transit S phase. The percentage of nuclei stained by uptake by BrdU was determined by immunostaining with anti-BrdU monoclonal antibodies as described by (Ohtsubo and Roberts, ibid.; Matsushime et al., ibid.; and Koff et al., ibid.; which are each incorporated by reference herein). The percent of cells staining positive for BrdU incorporation (percent labeled nuclei) was determined as a percentage of the total number of cells present on a 1 mm coverslip. The transfected cells were labeled with tritiated thymidine essentially as described above with the serum-starved cells being subjected to a three-hour pulse labeling with luCi/mo of tritiated thymidine. The percent of tritiated thymidine incorporation was determined as the percentage of tritiated thymidine incorporated (c.p.m.) into serum-starved and lipofected cells as compared to asynchronously proliferating cells pulse-labeled for three hours with tritiated thymidine. This confirmed that cells exposed to p27 antisense oligonucleotides continued to synthesize DNA for at least 24 hours following serum withdrawal. Of the serum starved cells treated with p27 antisense oligonucleotides, 35% incorporated BrdU into nuclear DNA, while only 2–3% of the cells treated with mismatch control oligonucleotides did so. Analogous results were obtained by using tritiated thymidine incorporation to measure DNA synthesis rates.

In sum, these results show that cells treated with p27 antisense oligonucleotides failed to induce p27 protein in response to mitogen depletion, and were unable to exit the cell cycle. Although the duration of the effect for this antisense preparation was limited, cells treated with p27 antisense expressed low levels of p27 protein and continued to proliferate for at least 48 hours without serum mitogens.

EXAMPLE III

The specificity of antisense oligonucleotides was demonstrated by showing that the effect of the antisense treatment could be overcome by restoring expression of the targeted protein.

The degeneracy of the genetic code was used to construct a p27 expression plasmid which could not be inhibited by the antisense oligonucleotides, but nevertheless encoded wild-type p27 protein (the p27 "wobble" plasmid):

[SEQ ID NO:5] (102) L A Q E S (106)

[SEQ ID NO:6] p27 Wild type CTG GCG CAG GAG AGC

[SEQ ID NO:7] p27 Wobble Mutant —T —A —A —A TCA

To construct the p27 "wobble" expression plasmid, a "megaprimer" was generated by PCR amplification using a primer to plasmid sequences (T7 primer) and a primer ([SEQ ID NO:8] 5'TAA AGG CAC CGC CTG GCG ACT ACC GCT GAC GTC CTG TGA TTC TTG TGC AAG CAC CTT GCA GGC GCT C-3') which contains mutations at the wobble positions for the amino acid sequence LAQESQD [SEQ ID NO:9] (amino acids 102–108) of murine p27. The "megaprimer" was subsequently used with a primer to plasmid sequences (T3 primer) at the 3' end to PCR amplify a full length clone which was subcloned into the expression vector pCS2+. These mutations created a p27 sequence with 7 unmatched bases to the p27 antisense oligonucleotide and created a unique Aat II site.

Figure 2A:
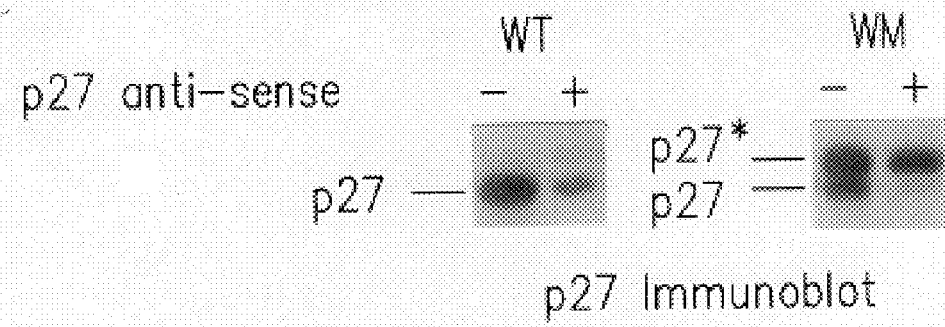
FIG. 2A is a p27 immunoblot analysis of proliferating Balb/c-3T3 cells 24 h after lipofection in the presence (+) or absence (−) of p27 antisense oligonucleotides with plasmid encoding either wild type p27 or tagged (p27*) p27 wobble mutant.

A "tagged" version of the p27 wobble plasmid was also constructed, which encoded an electrophoretic variant of p27 resulting from a single amino acid change outside of the domain targeted by the antisense oligonucleotide. In addition to the base changes listed above for amino acids 102–108, the p27 "tagged" wobble mutant also contained mutations at Serine (111) and Arginine (112). These amino acids were converted to Threonine and Serine, respectively resulting in a p27 wobble mutant that migrates slightly slower than endogenous murine p27 and exogenous wild type p27. The tagged p27 could be separated and thereby distinguished from endogenous p27, enabling a simultaneous test of the effects of p27 antisense oligonucleotides on expression from the wild type and wobble p27 genes in the same cell.

p27 immunoblot assay were carried out on extracts from proliferating Balb/c-3T3 cells twenty-four hours after lipofection in the presence or absence of p27 antisense oligonucleotides with plasmid encoding either wild type p27 or tagged p27 wobble mutant. It was observed that the p27 antisense oligonucleotides effectively inhibited expression from both an exogenous wild-type p27 gene, and from the endogenous p27 gene, but were unable to inhibit p27 protein expression from the p27 wobble plasmid (FIG. 2A).

Figure 2B:
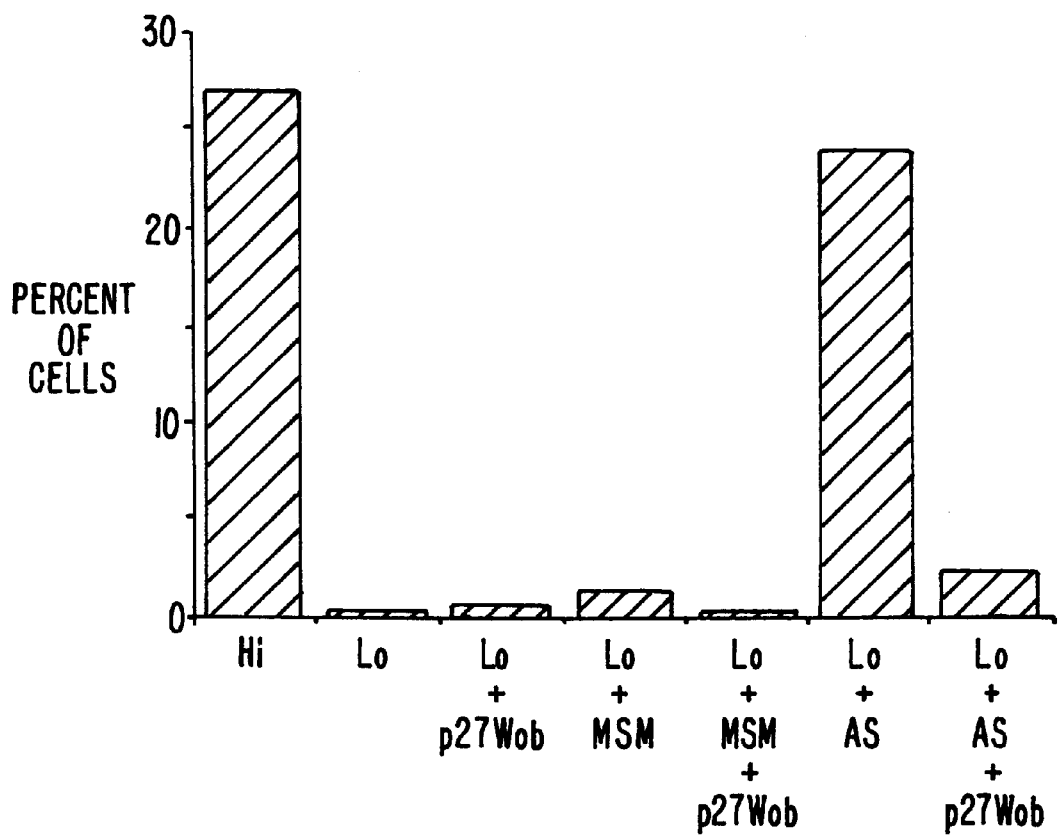
FIG. 2B shows results obtained when proliferating Balb/c-3T3 fibroblasts (Hi) were lipofected with p27 mismatch (MSM) or antisense (AS) oligonucleotides for 6 h in high serum.

A p27 wobble plasmid was then used to determine whether expression of p27 protein in the antisense treated cells renewed their responsiveness to mitogen depletion. These experiments were designed to study the physiological effects of p27 expression, and therefore used a wobble plasmid encoding fully wild type p27, rather than the electrophoretic variant described above. Balb/c-3T3 cells were lipofected with mismatch or p27 antisense oligonucleotides, and then microinjected with a both plasmid encoding β-galactosidase (to mark the injected cells) and with the p27 wobble plasmid. Microinjection, immunofluorescence staining, and fluorescence microscopy were carried out as described in Fisher et al., *Nuc. Acid Res.* 21:3857 (1993); Hanvey et al., *Science* 258: 1481 (1992); Wagner et al., *Science* 260:1510 (1993); Moulds et al., *Biochem.* 34:5044 (1995), each of which is incorporated herein by reference. Cells were rinsed once in serum-free medium and were then serum-starved in low serum medium containing 0.1% serum for 24 hours. As described above, the cells were pulse-labeled with BrdU for three hours followed by immunostaining for both BrdU and β-galactosidase. For costaining of β-galactosidase and BrdU, the cells were fixed, and then first incubated with a polyclonal anti-β galactosidase antibody (5'3' Inc. Boulder, Co.) for 60 minutes, followed by incubation with a fluorescein-conjugated goat anti-rabbit IgG (Jackson Immunoresearch Laboratories, West Grove, Pa.) for 30 minutes. The cells were then incubated with a fluorescein-conjugated rabbit anti-goat IgG antibody for 30 minutes. At the end of this procedure, the slides were fixed again with 3.7% formaldehyde for 10 minutes followed by incubation in acetone for 1 minute. The cells were rehydrated with TBS followed by a 10 minute treatment with 4N HCl and a final wash with TBS. To visualized the BrdU staining, the cells were incubated for 1 hour with a monoclonal anti-BrdU antibody (Boehringer Mannheim, Germany), followed by a 30 minute incubation with a rhodamine-conjugated donkey anti-mouse antibody (Jackson Immunoresearch Laboratories, West Grove, Pa.)). The percentage of cells in S phase measured by pulse labeling with BrdU which was carried out as described above. The percent of β-galactosidase positive cells that incorporated BrdU was determined and expressed as the percent of cells in S phase as compared to the total number of cells staining positive for β-galactosidase expression. Lipofection of cells with p27 antisense oligonucleotides markedly decreased the percentage of cells that withdrew from the cell cycle following mitogen depletion, and this was reversed by microinjection with the p27 wobble plasmid (FIG. 2B).

These results showed that the inability of p27 antisense treated cells to exit the cell cycle after mitogen depletion is specifically caused by the loss of p27 expression.

EXAMPLE IV

The basal level of p27 expressed in proliferating cells may contribute to an inhibitory threshold imposed on Cdk activation during G1 (Sherr and Roberts, *Genes & Dev.* 9:1149 (1995). In mitotically proliferating cells Cdk activation would thus occur when the number of cyclin-Cdk complexes exceeds the CKI threshold. Therefore, the time of Cdk activation during G1 would depend both upon the rate of cyclin synthesis and the level of CKI expression. (Overexpression of G1 cyclins causes early activation of cyclin-Cdk complexes, and a shorter G1. Ohtsubo and Roberts, *Science* 259:1908 (1993); Quelle et al., *Genes & Dev.* 7:1559 (1993); Resnitzky and Reed, *Mol Cell. Biol.* 15:3463 (1995)).

This Example describes experiments which indicate that a p27 threshold influences the timing of Cdk activation, and therefore the duration of G1. At one extreme, high levels of p27 have been shown to prevent Cdk activation and arrest the cell cycle in G1 (Polyak et al., *Cell* 78:59 (1994), Toyashima and Hunter, ibid., p. 67).

To determine whether decreased p27 expression allowed premature Cdk activation and a shortened G1, exponentially proliferating Balb/c-3T3 cells were lipofected with p27 antisense or mismatch control oligonucleotides and allowed to continue to proliferate in high serum for an additional 24 hours.

The p27 antisense treatment was observed to decrease p27 protein expression in proliferating cells well below the normal basal level, while no effect was seen on p27 expression in the mismatch control. Analysis of these cell populations by flow cytometry revealed that p27 antisense oligonucleotides markedly decreased the percentage of cells in G1, indicating that the length of G1 has been shortened relative to other phases of the cell cycle. This supports the conclusion that the level of p27 expressed in proliferating cells contributes to the length of G1.

EXAMPLE V

A targeted deletion of the p27 gene was created in transgenic mice and viable homozygous p27 "knock-out" animals were produced.

The knock-out mice, in which the p27 gene coding sequence was replaced with the neomycin resistance gene, were generated to determine the effect of such a deletion in homozygous and heterozygous mice. The genomic p27 sequences were derived from the 129/Sv strain of mice so that the homologous recombination could take place in a congenic background in 129/Sv mouse embryonic stem cells. A p27 genomic clone was isolated from a genomic library prepared from 129/Sv mice (Soriano et al., *Cell* 64:693–707 (1991); which is incorporated by reference herein) using a $^{32}$P-radiolabeled p27 cDNA probe. Plasmid pPNT (Tybulewicz et al., *Cell* 65:1153–1163 (1991), which is incorporated herein by reference in its entirety) containing the neomycin resistance gene (neo, a positive selection marker) and the Herpes simplex virus thymidine kinase gene (hsv-tk; a negative selection marker) under the control of the PGK promoter provided the vector backbone for the targeting construct. A 7 kb Xho I fragment containing the genomic 5' untranslated sequence of p27 was inserted at the Xho I site of the pPNT vector such that the 5' end of the p27 fragment was inserted upstream of the PGK promoter-neo expression cassette. A 1.8 kb Bgl II-Eco RI fragment containing the 3' untranslated p27 genomic sequence was inserted between Bgl II and Eco RI sites, downstream of the PGK promoter-neo expression cassette such that the 5' and 3' of the genomic fragments were in the same orientation. This resulted in a total of 8.8 kb of homology from the flanking regions of p27 with the entire p27 coding region being replaced by the PGK promoter-neo expression cassette from the pPNT vector. In this construct hsv-tk is also driven by the PGK promoter but lies 3' to the p27 flanking DNA and provides a means of selection against random integration events by causing cell death in the presence of 1(2-deoxy-2-fluoro-beta-D-arabinofuranosyl)-5-iodouracil (FIAU, a nucleoside analog).

The targeting construct was linearized and transfected by electroporation into mouse embryonic stem (ES) cells. A 129/Sv derived ES cell line, AK-7, described by Zhuang et al. (*Cell* 79:875–884 (1994); which is incorporated herein by reference in its entirety) was used for electroporation. These ES cells were routinely cultured on mitomycin C-treated (Sigma) SNL 76/7 STO cells (feeder cells) as described by McMahon and Bradley (*Cell* 62:1073–1085 (1990); which is incorporated herein by reference in its entirety) in culture medium containing high glucose DMEM supplemented with 15% fetal bovine serum (Hyclone) and 0.1 mM β-mercaptoethanol.

To prepare the targeting construct for transfection, 25 µg of the targeting construct was linearized by digestion with Hind III, phenol-chloroform extracted, and ethanol precipitated. The linearized vector was then electroporated into $10^7$ ES cells. The electroporated cells were seeded onto two gelatinized plates with a subconfluent layer of mitomycin-C inactivated SNL 76/7 STO feeder cells. Twenty-four hours post-electroporation, one plate received medium containing 0.2 mM G418 and the remaining plate received 0.2 mM G418 and 0.2 mM FIAU. The presence of FIAU provided approximately a 10-fold reduction in the number of colonies formed in comparison to control plates with G418 alone. The culture medium for each plate was changed every day for the first few days, and then changed as needed after selection had occurred. Colonies of ES cells with true homologous recombination (HR) events, in which p27 gene was replaced with the neo gene, were identified by the ability to amplify a 2 kb PCR fragment unique to the p27-knock-out construct. After 10 days of selection, a portion of each colony was picked microscopically with a drawn micropipette, and was directly analyzed by PCR as described by Joyner et al. (*Nature* 338:153–156 (1989); which is incorporated herein by reference in its entirety). Briefly, PCR amplification was performed as described (Kogan et al., *New England J. Med.* 317:985–990 (1987); which is incorporated herein by reference in its entirety) using 4 cycles of 93° C. for 30 seconds, 36 cycles of 93° C. for 30 seconds, 55° C. for 30 seconds, and 65° C. for 2 minutes. To detect the mutant p27 allele, primers neo-1 (CCT TCT ATG GCC TCC TTG ACG) and mgK2 (TTC TTA CCG AAA GGG ACA CTA ATC) [SEQ ID Nos:10 and 11, respectively] were used in the PCR reaction. Positive colonies, identified by PCR, were subcloned into 4-well plates, expanded into 60 mm plates and frozen into 2–3 ampules. Southern blot analysis using probes external to both the 5' and 3' end of the targeting construct confirmed that a true homologous recombination event had occurred in each of 12 clones surveyed.

To generate chimeric mice, 6 positive clones were trypsinized into single cells, and blastocysts obtained from C57BL/6J mice were each injected with approximately 15 cells from an individual clone. The injected blastocysts were then implanted into pseudopregnant F1 mice (C57BL/6J× 129/Sv). Chimeric pups with predominantly agouti coats (indicating a major contribution of the ES cells to the somatic tissues) were selected for further breeding. Nine complete male chimeras were subsequently identified representing three separate ES cell clones. The male chimeras were bred to C57BL/6J females. The chimeric males were also bred to 129/Sv females to place the knock-out mutation in a congenic background.

The transmission of the mutant p27 transgene in 50% of the F1 agouti progeny was again shown with PCR. Briefly, genomic DNA prepared from tail biopsies was subjected to PCR as described above using primers mgK-3 (TGG AAC CCT GTG CCA TCT CTA T) and neo-1 [SEQ ID Nos:12 and 10] to identify the mutant (p27 knock-out gene) and primers mgk-3 and mck-5 (GAG CAG ACG CCC AAG AAG C) [SEQ ID Nos:12 and 13] to identify the wild-type gene. Homozygous p27 deletions were obtained in the F2 generation as confirmed by the absence of a the ability to PCR a 0.5 kb fragment unique to the mutant transgene and the absence of a 0.9 kb wildtype fragment. The complete absence of p27 protein from these mice was confirmed on Western blots of whole tissue extracts using rabbit polyclonal anti-p27 antisera.

In a comparison of mice of each genotype (the homozygous knock-out, −/−; the heterozygous knock-out, ±; and wildtype, +/+) on the hybrid genetic background (129/Sv× C57BL/6J), a size difference between the homozygous p27 knock-out mice relative to wildtype mice was demonstrated. The hybrid mice (129/Sv×C57BL/6J) from the F2 generation displayed a considerable size variation because the wildtype 129/Sv mice are considerably larger than their C57BL/6J counterparts. However, the homozygous knockout mice displayed, on average, about 30% greater weight than sex matched wildtype litter mate controls. This difference was present at 3 weeks of age and persisted to adulthood ($p<0.05$). This size difference has been confirmed in the inbred (129/Sv) background.

To further examine the size difference between the knockout mice and the wildtype mice, internal organs from randomly selected knock-out mice and wildtype litter mate controls were dissected. The weights of internal organs of the knock-out mice were proportional to body size with the notable exception of the thymus and spleen, which on the average were approximately twice as large in the knock-out animals. Counts of nucleated cells from the spleen and thymus from the knock-out mice confirmed the hypercellularity of these tissues and were proportional to the weights of the organs. p27 has been shown to be expressed both in the cortex and the more mature medullary areas of the mouse thymus. The increased mass of the thymus and spleen, however, was small in comparison to the overall body weight of the animal and therefore did not account for the weight difference of the animals as a whole. Thus, the p27 deletion appeared to lead to an overall increase in the animals size, without a disproportionate increase in fat or organomegaly.

Splenic CFU-Meg (megakaryocyte colony forming unit), CFU-GM (granulocyte/macrophage colony forming unit), BFU-E (erythroid burst forming unit) were determined on spleens harvested from two wildtype and two homozygous knock-out mice (that were less than a factor of two different in size in weight and total cell number) by colony-forming units assay essentially as described (Kaushansky et al. *Nature* 369:568–571 (1994); Broudy et al., *Blood* 85:1719–1726 (1995); Kaushansky et al., *J. Clin. Invest.* 96:1683–1687 (1995), which are incorporated herein by reference). A comparison of the total number of CFU-Meg, CFU-GM, BFU-E from the spleens of the knock-out and wildtype mice demonstrated a 10-fold increase in the number of each of the cell types in the spleens from the knock-out mice relative to the number of each cell type from the spleens of the wildtype mice.

Western blots of normal murine ES cell extracts reveals p27 expression even at this early stage of mouse development. Western blots detected p27 expression in normal mouse tissues, including a diffuse pattern of expression in thymic tissue. No detectable p27 expression was seen in Western blots of tissues from knock-out mice.

Although the foregoing invention has been described in some detail by way of illustration and example for purposes of clarity of understanding, it will be obvious that certain changes and modifications may be practiced within the scope of the appended claims.

What is claimed is:

1. A method for increasing the proportion of dividing cells in a vertebrate cell population comprising:

exposing said population of cells to an inhibitor of p27 in an amount sufficient to increase the proportion of dividing cells to non-dividing cells relative to said proportion in a population of untreated cells.

2. The method according to claim 1, wherein the cell population is a substantially non-dividing or terminally differentiated primary cell population.

3. The method according to claim 1, wherein the cell population comprises fibroblasts, osteoblasts, myeloblasts, neurons or epithelial cells.

4. The method according to claim 1, wherein the cell population comprises hematopoietic progenitor cells.

5. The method according to claim 1, wherein the exposing step is performed in vitro.

6. The method according to claim 5, further comprising the step of contacting said cell population with a vector which comprises a nucleic acid sequence encoding a desired gene product.

7. The method according to claim 6, wherein the vector which comprises a nucleic acid sequence encoding a desired gene product is a genetically modified virus.

8. The method according to claim 7, wherein the genetically modified viral vector is a retroviral vector.

9. The method according to claim 8, wherein the cell population comprises hematopoietic progenitor cells.

10. The method according to claim 9, further comprising the step of:

administering the exposed hematopoietic progenitor cells contacted with the retroviral vector to a host for expression of the desired gene.

11. The method according to claim 1, wherein the inhibitor is an oligonucleotide that specifically inhibits p27 expression in said cell population.

12. The method of claim 11, wherein the oligonucleotide is an antisense oligonucleotide.

13. The method according to claim 1, wherein the vertebrate cell is a mammalian cell.

14. The method according to claim 13, wherein the mammalian cell is a human cell.

15. A method for increasing the efficiency of transducing a vertebrate cell population with a viral vector encoding a gene product of interest, comprising:

exposing said population of cells to an inhibitor of p27 in an amount sufficient to increase the proportion of dividing cells to non-dividing cells relative to said proportion in a population of untreated cells, and contacting said exposed cells to a viral vector encoding the gene product of interest.

16. The method according to claim 15, wherein the vertebrate cell is a mammalian hematopoietic progenitor cell.

17. An inhibitor of p27 which comprises an oligonucleotide that specifically binds to DNA encoding p27 or RNA transcribed therefrom and inhibits expression of p27 protein.

18. The inhibitor of claim 17, wherein the oligonucleotide is an antisense oligonucleotide.

19. An isolated vertebrate cell population which has been treated with an inhibitor of p27 and having an increased proportion of dividing cells to non-dividing cells relative to said proportion in a population of untreated cells.

20. The isolated cell population of claim 19 which comprises hematopoietic progenitor cells.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:1:

UGGCUCUCCU GCGCC                                                     15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:2:

UCCCUUUGGC GCGCC                                                    15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:3:

GCGUCUGCUC CACAG                                                    15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:4:

GCAUCCCCUG UGCAG                                                    15

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Leu Ala Gln Glu Ser
1               5

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:6:

CTGGCGCAGG AGAGC                                                    15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:7:

CTTGCACAAG AATCA                                                    15

(2) INFORMATION FOR SEQ ID NO:8:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:8:

```
TAAAGGCACC GCCTGGCGAC TACCGCTGAC GTCCTGTGAT TCTTGTGCAA GCACCTTGCA        60

GGCGCT                                                                   66
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Leu Ala Gln Glu Ser Gln Asp
1               5
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:10:

```
CCTTCTATGG CCTCCTTGAC G                                                  21
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:11:

```
TTCTTACCGA AAGGGACACT AATC                                               24
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleotide (xi) SEQUENCE DESCRIPTION: SEQ ID NO:12:

```
TGGAACCCTG TGCCATCTCT AT                                                 22
```

(2) INFORMATION FOR SEQ ID NO:13:

```
(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleotide (xi) SEQUENCE DESCRIPTION: SEQ ID NO:13:

GAGCAGACGC CCAAGAAGC                                                    19
```